US011938467B2

(12) United States Patent
Piromchart et al.

(10) Patent No.: US 11,938,467 B2
(45) Date of Patent: Mar. 26, 2024

(54) CATALYST SYSTEM FOR PRODUCING CYCLIC CARBONATES AND METHOD RELATED THERETO

(71) Applicant: PTT EXPLORATION AND PRODUCTION PUBLIC COMPANY LIMITED, Bangkok (TH)

(72) Inventors: Taradon Piromchart, Bangkok (TH); Valerio D'Elia, Rayong (TH)

(73) Assignee: PTT EXPLORATION AND PRODUCTION PUBLIC COMPANY LIMITED, Bangkok (TH)

( * ) Notice: Subject to any disclaimer, the term of this patent is extended or adjusted under 35 U.S.C. 154(b) by 434 days.

(21) Appl. No.: 17/206,077

(22) Filed: Mar. 18, 2021

(65) Prior Publication Data

US 2021/0205798 A1 Jul. 8, 2021

Related U.S. Application Data

(63) Continuation of application No. PCT/TH2019/000041, filed on Sep. 18, 2019.

(Continued)

(51) Int. Cl.

| | |
|---|---|
| ***B01J 31/02*** | (2006.01) |
| ***B01J 21/08*** | (2006.01) |
| ***B01J 23/18*** | (2006.01) |
| ***B01J 31/12*** | (2006.01) |
| ***B01J 35/12*** | (2006.01) |

(Continued)

(52) U.S. Cl.

CPC ........... *B01J 31/0268* (2013.01); *B01J 21/08* (2013.01); *B01J 23/18* (2013.01); *B01J 31/0239* (2013.01); *B01J 31/0279* (2013.01); *B01J 31/0298* (2013.01); *B01J 31/121* (2013.01); *B01J 35/12* (2013.01); *B01J 37/04* (2013.01); *B01J 37/08* (2013.01); *C07F 7/1804* (2013.01); *C07D 317/36* (2013.01)

(58) Field of Classification Search

CPC ........ B01J 21/08; B01J 23/18; B01J 31/0239; B01J 31/0268; B01J 31/0279; B01J 31/0284; B01J 31/0295; B01J 31/0298; B01J 31/121; B01J 31/26; B01J 35/12; B01J 37/04; B01J 37/08; B01J 2231/34; C07D 317/36; C07F 7/1804

See application file for complete search history.

(56) References Cited

U.S. PATENT DOCUMENTS

| | | | |
|---|---|---|---|
| 2,773,070 | A | 12/1956 | Lichtenwalter et al. |
| 2015/0119584 | A1 | 4/2015 | Yeh et al. |
| 2016/0145233 | A1 | 5/2016 | D'Elia et al. |

OTHER PUBLICATIONS

International Search Report and Written Opinion dated Mar. 6, 2020 in connection with International Application No. PCT/TH2019/000041, 10 pages.

(Continued)

*Primary Examiner* — Brian A McCaig

(74) *Attorney, Agent, or Firm* — Baker & McKenzie LLP

(57) ABSTRACT

The present invention provides a catalyst system for producing cyclic carbonates from carbon dioxide ($CO_2$) and epoxide-based compounds comprising:

a pre-catalyst; and a co-catalyst wherein said pre catalyst is $BiCl_3$ and said co-catalyst is selected from tetra-n-butylammonium bromide (TBAB), tetra-n-butylammonium iodide (TBAI), tetra-n-butylphosphonium bromide ($PBu_4Br$), tetra-n-butylphosphonium iodide ($PBu_4I$) or mixtures thereof.

16 Claims, 1 Drawing Sheet

Related U.S. Application Data

(60) Provisional application No. 62/732,987, filed on Sep. 18, 2018.

(51) Int. Cl.

| | |
|---|---|
| ***B01J 37/04*** | (2006.01) |
| ***B01J 37/08*** | (2006.01) |
| ***C07F 7/18*** | (2006.01) |
| *C07D 317/36* | (2006.01) |

(56) References Cited

OTHER PUBLICATIONS

Dai Weili et al.: "A mini review on chemical fixation of CO2: Absorption and catalytic conversion into cyclic carbonates", Frontiers of Chemica Engineering in China, Gaodeng Jiaoyu Chubanshe, CN, vol. 4, No. 2, Sep. 25, 2009, 9 pages.

Taradon Piromchart et al.: "The Conversion of Waste CO2 to Intermediated Petrochemical Product", International Petroleum Technology Conference, Mar. 22, 2019, 8 pages.

CATALYST SYSTEM FOR PRODUCING CYCLIC CARBONATES AND METHOD RELATED THERETO

CROSS-REFERENCE TO RELATED APPLICATIONS

This application is a continuation of and claims priority to International Application No. PCT/TH2019/000041, filed on Sep. 18, 2019, titled "Catalyst System for Producing Cyclic Carbonates and Method Related Thereto," which claims priority to U.S. Provisional Application No. 62/732,987 filed on Sep. 18, 2018, all of which are incorporated by reference in their entirety for all purposes.

FIELD OF INVENTION

This invention relates to a catalyst system for producing cyclic carbonates, and a method for preparation of the cyclic carbonates by using the catalyst system.

BACKGROUND OF INVENTION

Carbon dioxide ($CO_2$) emissions, such as from industrial processes and fuel combustion, are becoming a serious problem worldwide because such emissions are considered a primary driver of climate change. According to the Global Energy & $CO_2$ Status Report 2017 launched by the International Energy Agency (IEA), global energy-related $CO_2$ emissions reached a historic high of 32.5 gigatonnes. Legislators around the globe have started to set limitations on the unrestricted release of $CO_2$ in the atmosphere. Among approaches to solve the problem, the chemical transformation of $CO_2$ into high value chemicals has attracted considerable attention in recent years. Cyclic carbonates are one of those because they can be easily produced from the cycloaddition of $CO_2$ to epoxides under mild conditions. Cyclic carbonates are at the center of a multibillion USD market that involves polycarbonates, glycols, and polyesters. However, $CO_2$ is kinetically and thermodynamically stable, thus it requires a large amount of energy to transform $CO_2$ into other chemicals, including cyclic carbonates. As such, a promising approach is to develop effective catalysts that allow for higher conversion of $CO_2$ at lower temperatures.

Cyclic carbonates are produced from $CO_2$ by cycloaddition reaction to epoxides. Several catalyst systems exist to carry out such reaction, however, very few of such systems are capable of operating using impure $CO_2$ under ambient conditions. The ability to capture $CO_2$ from gas mixtures is advantageous as it can be easily applied with flue gas and is therefore commercially attractive for cyclic carbonate production. Examples of said catalysts include a bimetallic aluminium (salen) complex disclosed in Energy Environ. Sci., 2010, 3, 212-215 which is used for cyclic carbonate production with $CO_2$ having moisture and NOx as impurities in $CO_2$. However, said complex has a very high molecular weight and its preparation involves several synthetic steps because of the elaborated structure of organic framework-coordinating aluminum atoms.

U.S. Pat. No. 9,586,926 B2 disclosed a method for producing cyclic carbonate from carbonation of epoxide by $CO_2$. The method is performed via a homogeneous catalyst system comprising a pre-catalyst selected from $YCl_3$, $Y_2O_3$, $Y(NO_3)_3$, $ScCl_2$, or $LaCl_3$ and a co-catalyst selected from tetrabutylammonium bromide, 4-dimethylaminopyridine, or bis(triphenylphosphine) iminium chloride at a mole ratio in the range of 1:1 to 1:2. However, the catalytic activity of this system with impure or diluted $CO_2$ is relatively low under ambient conditions.

Monteiro, et. al. (Applied Catalysis A: General (2017), 544 (25), 46-54) disclosed a catalyst system comprising 1-methyl-3-(3-trimethoxysilylpropyl) imidazolium chloride ionic liquid catalyst supported on titanate nanotubes (TNT) or nanowires (TNW) as a pre-catalyst and $ZnBr_2$ as a co-catalyst for synthesizing cyclic carbonates. Although selectivity of the catalyst to $CO_2$ is high, the catalyst was used only at high pressures of pure $CO_2$ and not with diluted $CO_2$ Therefore, there is a need to develop a new generation of catalyst system to produce cyclic carbonates from $CO_2$, especially the diluted and/or impure $CO_2$, under mild conditions with a high catalytic activity and high selectivity. Accordingly, the present invention is intended to provide a catalyst system for the conversion of $CO_2$ and epoxides to cyclic carbonates under mild conditions using pure and impure $CO_2$ having a high catalytic activity and being cost-effective.

SUMMARY OF THE INVENTION

In one embodiment, the present invention relates to a catalyst system for producing cyclic carbonates from carbon dioxide ($CO_2$) and epoxide-based compounds comprising:

a pre-catalyst; and a co-catalyst wherein said pre catalyst is $BiCl_3$ and said co-catalyst is selected from tetra-n-butylammonium bromide (TBAB), tetra-n-butylammonium iodide (TBAI), tetra-n-butylphosphonium bromide ($PBu_4Br$), tetra-n-butylphosphonium iodide ($PBu_4I$) or mixtures thereof.

In another embodiment of the invention, the present invention relates to a method for producing cyclic carbonates, which comprises reacting epoxide-based compounds with carbon dioxide in the presence of a catalyst system comprising:

a pre-catalyst; and a co-catalyst wherein said pre catalyst is $BiCl_3$ and said co-catalyst is selected from tetra-n-butylammonium bromide (TBAB), tetra-n-butylammonium iodide (TBAI), tetra-n-butylphosphonium bromide ($PBu_4Br$), tetra-n-butylphosphonium iodide ($PBu_4I$) or mixtures thereof; and wherein said method is performed using a mole ratio of the pre-catalyst:the co-catalyst:the epoxide-based compounds in the range of about 1:1:10 to 1:3:100; at a pressure of carbon dioxide in the range of about 1 to 100 bar; a temperature in the range of about 10 to 200° C.; and a reaction time in the range of about 1 to 8 hours.

DETAILED DESCRIPTION OF THE INVENTION

Figure 1:
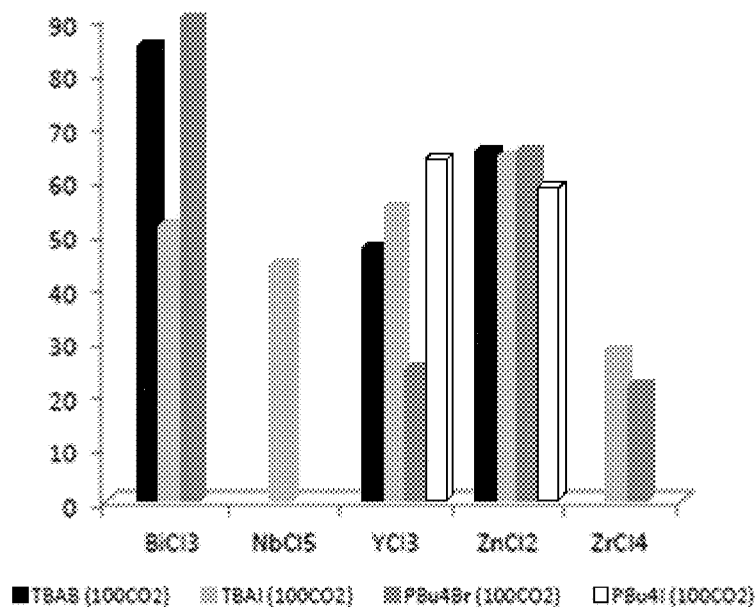
FIG. 1. The conversion of propylene oxide to propylene carbonate determined by $^1H$ NMR for various catalyst systems under ambient conditions using pure $CO_2$ at room temperature and pressure of 1 bar.

The present invention provides a catalyst system for producing cyclic carbonates with cost-effectiveness and high catalytic activity for conversion of $CO_2$ and epoxide-based compounds to cyclic carbonates. Also, the present invention provides a method of making the cyclic carbonates by using the catalyst system with mild conditions using pure and impure $CO_2$. Details of the present invention can be elucidated according to the specification as follows.

Technical terms or scientific terms used herein have definitions as understood by those having an ordinary skill in the art, unless stated otherwise.

Equipment, apparatus, methods, or chemicals mentioned here means equipment, apparatus, processes, or chemicals commonly operated or used by those skilled in the art, unless explicitly stated otherwise that they are equipment, apparatus, methods, or chemicals specifically used in this invention.

The use of the singular or plural nouns with the term "comprising" in the claims or in the specification refers to "one" and also "one or more," "at least one," and "one or more than one."

All compositions and/or processes disclosed and claimed are aimed to include aspects of the invention from actions, operation, modifications, or changing of any parameters without performing significantly different experiments from this invention, and obtaining similar objects with the same utilities and results of the present invention according to persons skilled in the art although without mention of the claims specifically. Therefore, substitution or similar objects to the present invention including minor modifications or changes which can be clearly seen by persons skilled in the art should be considered within the scope, spirit, and concept of the invention as appended claims.

Throughout this application, the term "about" is used to indicate that any value presented herein may potentially vary or deviate. Such variation or deviation may result from errors of apparatus, methods used in calculation, or from individual operator implementing apparatus or methods. These include variations or deviations caused by changes of the physical properties.

Following is a detailed description of the invention without any intention to limit the scope of the invention.

According to one embodiment of the invention, the present invention provides a catalyst system for producing cyclic carbonates comprising:

a pre-catalyst; and a co-catalyst wherein said pre catalyst is $BiCl_3$ and said co-catalyst is selected from tetra-n-butylammonium bromide (TBAB), tetra-n-butylammonium iodide (TBAI), tetra-n-butylphosphonium bromide ($PBu_4Br$), tetra-n-butylphosphonium iodide ($PBu_4I$) or mixtures thereof.

In a preferred exemplary embodiment, the co-catalyst is selected from tetra-n-butylammonium iodide (TBAI) or tetra-n-butylphosphonium bromide ($PBu_4Br$).

In another exemplary embodiment, the mole ratio between the pre-catalyst and the co-catalyst is in the range of about 1:1 to 1:3.

In a preferred exemplary embodiment, the mole ratio between the pre-catalyst and the co-catalyst is at 1:2.

In another embodiment of the invention, this invention relates to a use of the catalyst system of the invention for producing cyclic carbonates from $CO_2$ and epoxide-based compounds.

In another embodiment of the invention, the present invention provides a method for producing cyclic carbonates which comprises reacting epoxide-based compounds with carbon dioxide in the presence of a catalyst system comprising:

a pre-catalyst; and a co-catalyst;

wherein said pre catalyst is $BiCl_3$ and said co-catalyst is selected from tetra-n-butylammonium bromide (TBAB), tetra-n-butylammonium iodide (TBAI), tetra-n-butylphosphonium bromide ($PBu_4Br$), tetra-n-butylphosphonium iodide ($PBu_4I$) or mixtures thereof; and wherein said method is performed using a mole ratio of the pre-catalyst:the co-catalyst the epoxide-based compounds in the range of about 1:1:10 to 1:3:100; at a pressure of carbon dioxide in the range of about 1 to 100 bar; a temperature in the range of about 10 to 200° C.; and a reaction time in the range of about 1 to 8 hours.

In another exemplary embodiment, a mole ratio of the pre-catalyst:the co-catalyst:the epoxide-based compounds is in the range of about 1:1:10 to 1:3:50.

In a preferred exemplary embodiment, a mole ratio of the pre-catalyst:the co-catalyst:the epoxide-based compounds is at about 1:2:50.

In another exemplary embodiment, the pressure of carbon dioxide is in the range from about 1 to 50 bar.

In a preferred exemplary embodiment, the pressure of carbon dioxide is in the range of about 1 to 10 bar.

In another exemplary embodiment, temperature is in the range from about 25 to 200° C.

In a preferred exemplary embodiment, the temperature is in the range of about 25 to 120° C.

In another exemplary embodiment, the reaction time is in the range of about 1 to 6 hours.

In a preferred exemplary embodiment, the reaction time is in the range of about 2 to 4 hours.

In a preferred exemplary embodiment, the co-catalyst is selected from tetra-n-butylammonium iodide (TBAI) or tetra-n-butylphosphonium bromide (PBu4Br).

Hereafter, examples of the invention are shown without any purpose to limit any scope of the invention.

Example

Chemicals and Consumables

All chemicals were purchased from commercial sources and used as received. Early transition metal halides were stored and handled inside a glovebox. Metal-free compounds were stored in chemical cabinets and used without further precautions. Pure and diluted $CO_2$ ($CO_2$ at a concentration of about 50% in air) were received in metal cylinders and dosed via regulator.

Cyclic Carbonate Synthesis Under Ambient Conditions (Room Temperature, $CO_2$)

The experiments were carried out in a 100 mL three-neck round-bottom flask. The catalyst (about 2 mmol) and the co-catalyst (about 4 mmol) were added to the reaction vessel with a magnetic stir bar. A balloon filled with about 2 L of $CO_2$ (or diluted $CO_2$ at a concentration of about 50% in air) was connected to the flask along with an in-situ infrared probe. The reactions were initialized with addition of about 100 mmol of propylene oxide and stirred at about 800 rpm for about 3 hours. The products were diluted with deuterated chloroform ($CDCl_3$) and identified by $^1H$ NMR.

Cyclic Carbonate Synthesis Using Autoclave (Pressure>1 Bar)

The experiments were carried out in a 75 mL autoclave. The reactions were prepared in a glove box by adding about 2 mmol of catalyst and about 4 mmol of co-catalyst and about 100 mmol of propylene oxide into the autoclave equipped with a magnetic stir bar. The reactions were initialized with the addition of $CO_2$. The autoclave was set in an oil-bath at the target temperatures and stirred at about 800 rpm. After about 3 hours, the vessel was allowed to cool to room temperature. The propylene carbonate obtained from the reaction was identified by $^1$H-NMR in $CDCl_3$.

Initial Catalytic Screening with Pure $CO_2$

Figure 2:
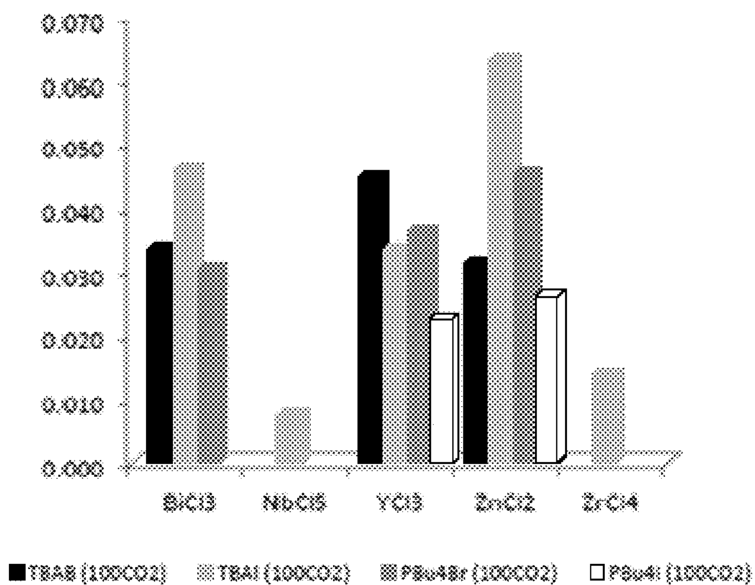
FIG. 2. The initial rate of formation of propylene carbonate determined by in situ IR for various catalyst systems under ambient conditions using pure $CO_2$ at room temperature and pressure of 1 bar.

The homogeneous catalyst systems (pairs of metal halides, and ammonium or phosphonium salts) underwent an initial screening procedure under ambient conditions (room temperature, under pressure about 1 bar of $CO_2$ filled in balloon with a needle) for about 3 hours for the cycloaddition reaction of $CO_2$ to propylene oxide to obtain propylene carbonate. The conversion of propylene oxide to propylene carbonate in the reaction time of about 3 hours is shown in FIG. 1. The initial rate of propylene carbonate formation, measured by in situ infrared probe in the first 15 minutes of reaction, is shown in FIG. 2.

Based on the observed results, it appeared that $BiCl_3$/$PBu_4Br$ provided the highest conversion under ambient conditions with pure $CO_2$ in the reaction time of about 3 hours (FIG. 1). Considering the initial rates of propylene carbonate formation, instead (FIG. 2), $ZnCl_2$/TBAI showed the highest initial rate. $BiCl_3$/TBAI and $YCl_3$/TBAB displayed slightly lower initial rates than $ZnCl_2$/TBAI. Taking together the results from the conversion in about 3 hours and the initial rates, it appeared that metal-based systems such as $BiCl_3$/$PBu_4Br$, $BiCl_3$/TBAI, $YCl_3$/TBAB and $ZnCl_2$/TBAI presented the most promising performance. In particular, $BiCl_3$ based catalyst for the cycloaddition of $CO_2$ to epoxides has not been reported earlier. For these reasons, the following experiments would be focused on metal based catalysts.

Catalytic Screening with $CO_2$ at a Concentration of about 50% Under Ambient Conditions After the initial screening under ambient conditions with pure $CO_2$, the use of diluted $CO_2$ (concentration of about 50% in air) was studied. The results of this screening are presented in Table 1.

From Table 1, the data suggests that $BiCl_3$/$PBu_4Br$ and $ZnCl_2$/TBAI are the best homogeneous candidates to promote the conversion of propylene oxide to propylene carbonate.

TABLE 1

Conversion of propylene oxide to propylene carbonate using diluted $CO_2$ (concentration of about 50%)

| Catalyst system | $CO_2$ concentration (%) | % Conversion (at about 3 hours) | Initial rate (a.u.) |
|---|---|---|---|
| $BiCl_3$/TBAI | 100 | 52 | 0.046 |
| $BiCl_3$/TBAI | 50 | 6 | 0.022 |
| $BiCl_3$/$PBu_4Br$ | 100 | 90 | 0.030 |
| $BiCl_3$/$PBu_4Br$ | 50 | 61 | 0.018 |
| $YCl_3$/TBAI | 100 | 55 | 0.034 |
| $YCl_3$/TBAI | 50 | 4 | 0.005 |
| $YCl_3$/$PBu_4Br$ | 100 | 25 | 0.036 |
| $YCl_3$/$PBu_4Br$ | 50 | 2 | 0.006 |
| $ZnCl_3$/TBAI | 100 | 64 | 0.063 |
| $ZnCl_3$/TBAI | 50 | 4 | 0.033 |
| $ZnCl_3$/$PBu_{4B}r$ | 100 | 65 | 0.046 |
| $ZnCl_3$/$PBu_4Br$ | 50 | 4 | 0.019 |

Catalytic Screening with Pure and $CO_2$ at a Concentration of about 50% in Autoclave Following the study under ambient conditions with pure and diluted $CO_2$, the attention was focused on optimizing the catalytic activity under several reaction conditions with the temperatures ranging from room temperature to about 120° C. and the pressure of pure and diluted $CO_2$ (concentration of about 50% in air) from about 5 to 10 bar. The results are shown in Table 2.

TABLE 2

Reactions in autoclave using $BiCl_3$, $YCl_3$ and $ZnCl_2$ under various conditions.

| Catalyst system | Pressure (bar)/ temperature (° C.) | $CO_2$ concentration (%) | % Conversion of $CO_2$ (at about 3 hours) |
|---|---|---|---|
| $BiCl_3$/TBAI | 10/RT | 100 | complete |
| $BiCl_3$/TBAI | 10/80 | 100 | complete in 10 minutes |
| $BiCl_3$/TBAI | 10/60 | 100 | 31 |
| $BiCl_3$/TBAI | 10/RT | 50 | 40 |
| $BiCl_3$/TBAI | 10/60 | 50 | 75 |
| $BiCl_3$/TBAI | 10/80 | 50 | complete |
| $BiCl_3$/TBAI | 10/100 | 50 | 60 |
| $BiCl_3$/TBAI | 10/120 | 50 | 80 |
| $BiCl_3$/TBAI | 5/60 | 50 | 12 |
| $BiCl_3$/TBAI | 5/120 | 50 | 35 |
| $BiCl_3$/TBAI | 7/120 | 50 | 40 |
| $BiCl_3$/$PBu_4Br$ | 10/80 | 50 | 52 |
| $BiCl_3$/$PBu_4Br$ | 10/100 | 50 | 67 |
| $YCl_3$/TBAI | 10/RT | 100 | complete |
| $YCl_3$/TBAI | 10/80 | 100 | complete |
| $YCl_3$/TBAI | 10/RT | 50 | 27 |
| $YCl_3$/TBAI | 10/80 | 50 | complete |
| $ZnCl_3$/TBAI | 10/RT | 100 | complete |
| $ZnCl_3$/TBAI | 10/80 | 100 | complete in 10 minutes |
| $ZnCl_3$/TBAI | 10/RT | 50 | 27 |
| $ZnCl_3$/TBAI | 10/80 | 50 | 96 |
| $ZnCl_3$/TBAI | 10/60 | 50 | complete |

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

BEST MODE OF THE INVENTION

Best mode of the invention is as provided in the description of the invention.

The invention claimed is:

1. A method for producing cyclic carbonates which comprises reacting epoxide-based compounds with carbon dioxide ($CO_2$) in the presence of a catalyst system comprising:

a pre-catalyst; and a co-catalyst wherein said pre catalyst is $BiCl_3$ and said co-catalyst is selected from tetra-n-butylammonium bromide (TBAB), tetra-n-butylammonium iodide (TBAI), tetran-butylphosphonium bromide ($PBu_4Br$), tetra-n-butylphosphonium iodide ($Pbu_4I$) or mixtures thereof; and wherein said method is performed using a mole ratio of the pre-catalyst:the co-catalyst:the epoxide-based compound in the range of 1:1:10 to 1:3:50; at a pressure of carbon dioxide in the range of 1 to 100 bar; a temperature in the range of 10 to 200° C.; and a reaction time in the range of 1 to 8 hours.

2. The method according to claim 1, wherein the method is performed using the pressure of carbon dioxide in the range of 1 to 50 bar.

3. The method according to claim 2, wherein the pressure of carbon dioxide is in the range of 1 to 10 bar.

4. The method according to claim 1, wherein the temperature in the range of 25 to 200° C.

5. The method according to claim 4, wherein the temperature is in the range of 25 to 120° C.

6. The method according to claim 1, wherein the reaction time is in the range of 1 to 6 hours.

7. The method according to claim 6, wherein the reaction time is in the range of 2 to 4 hours.

8. The method according to claim 1, wherein the co-catalyst is selected from tetra-n-butylammonium iodide (TBAI) or tetra-n-butylphosphonium bromide ($Pbu_4Br$).

9. A method for producing cyclic carbonates which comprises reacting epoxide-based compounds with carbon dioxide ($CO_2$) in the presence of a catalyst system comprising:

a pre-catalyst; and a co-catalyst wherein said pre catalyst is $BiCl_3$ and said co-catalyst is selected from tetra-n-butylammonium bromide (TBAB), tetra-n-butylammonium iodide (TBAI), tetra-n-butylphosphonium bromide ($Pbu_4Br$), tetra-n-butylphosphonium iodide ($Pbu_4I$) or mixtures thereof; and wherein said method is performed using a mole ratio of the pre-catalyst:the co-catalyst:the epoxide-based compound of 1:2:50; at a pressure of carbon dioxide in the range of 1 to 100 bar; a temperature in the range of 10 to 200° C.; and a reaction time in the range of 1 to 8 hours.

10. The method according to claim 9, wherein the method is performed using the pressure of carbon dioxide in the range of 1 to 50 bar.

11. The method according to claim 10, wherein the pressure of carbon dioxide is in the range of 1 to 10 bar.

12. The method according to claim 9, wherein the temperature in the range of 25 to 200° C.

13. The method according to claim 12, wherein the temperature is in the range of 25 to 120° C.

14. The method according to claim 9, wherein the reaction time is in the range of 1 to 6 hours.

15. The method according to claim 14, wherein the reaction time is in the range of 2 to 4 hours.

16. The method according to claim 9, wherein the co-catalyst is selected from tetra-n-butylammonium iodide (TBAI) or tetra-n-butylphosphonium bromide ($Pbu_4Br$).

* * * * *